(12) United States Patent
Lifshitz-Liron

(10) Patent No.: US 7,393,967 B2
(45) Date of Patent: Jul. 1, 2008

(54) PROCESS FOR THE PREPARATION OF CINACALCET BASE

(75) Inventor: Revital Lifshitz-Liron, Hertzlia (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/796,395

(22) Filed: Apr. 27, 2007

(65) Prior Publication Data

US 2007/0260091 A1 Nov. 8, 2007

Related U.S. Application Data

(60) Provisional application No. 60/799,443, filed on May 10, 2006, provisional application No. 60/796,317, filed on Apr. 27, 2006.

(51) Int. Cl.
*C07C 229/00* (2006.01)
(52) U.S. Cl. ............................. 560/41; 560/28; 514/487
(58) Field of Classification Search .................. 560/41, 560/28; 514/487
See application file for complete search history.

(56) References Cited

U.S. PATENT DOCUMENTS

| 4,966,988 | A | 10/1990 | Schinski et al. |
|---|---|---|---|
| 5,648,541 | A | 7/1997 | VanWagenen et al. |
| 6,011,068 | A | 1/2000 | Nemeth et al. |
| 6,031,003 | A | 2/2000 | Nemeth et al. |
| 6,211,244 | B1 | 4/2001 | Van Wagenen et al. |
| 6,313,146 | B1 | 11/2001 | Van Wagenen et al. |
| 2005/0147669 | A1 | 7/2005 | Lawrence et al. |
| 2005/0234261 | A1 | 10/2005 | Wilken et al. |
| 2006/0276534 | A1 | 12/2006 | Martin et al. |

FOREIGN PATENT DOCUMENTS

WO WO 2006/125026 11/2006

OTHER PUBLICATIONS

"Cinacalcet Hydrochloride: Treatment of Hyperparathyroidism", Drugs of the Future (2002) 27 (9):831-836.
Wang et al., "Synthesis of Cinacalcet congeners", Tetrahedron Letters (2004) 45:8355-8358.
Devasher et al., "Aqueous-Phase, Palladium-catalyzed cross-coupling of aryl bromides under mild conditions, using water soluable, sterically demanding alkyphosphines", Journal of Organic Chemistry, American Chemical Society, vol. 69, 2004, pp. 7919-7927.
Battistuzzi et al. "An Efficient Palladium-Catalyzed Synthesis of Cinnamaldehydes from Acrolein Diethyl Acetal and Aryl Iodides and Bromides" *Organic Letters*, vol. 5, pp. 777-780, (2003).
Berthiol et al. "Direct Synthesis of Cinnamaldehyde Derivatives by Reaction of Aryl Bromides with 3,3-Diacetoxypropene Catalyzed by a Palladium-Tetraphosphine Complex" *Catalysis Letters* vol. 102, Nos. 3-4, pp. 281-284, (2005).
Soai et al. "Sodium Borohydride-t-Butyl Alcohol-Methanol as an Efficient System for the Selective Reduction of Esters" *Snthetic Communication*, vol. 12 (6), pp. 463-467, (1982).
Streitwieser, *Introduction to Organic Chemistry*, Ch 15, pp. 376-403, (1976); MacMillan Publishing Co., Inc., New York.
Battistuzzi et al. "3-Arylpropanoate Esters through the Palladium-Catalyzed Reaction of Aryl Halides with Acrolein Diethyl Acetal" Synlett, No. 8, pp. 1133-1136, (2003).
"Sensipar (Cinacalcet HCI) Tablets" Summary Basis of Approval of New Drug Application #21-688 by FDA, (2004).
Iqbal et al.., "Cinacalcet Hydrochloride" *IDrugs*, vol. 6, No. 6, pp. 587-592, (2003).
Synder, L.R. et al., *Introduction to Modern Liquid Chromatography*, 2nd Ed., (1979), pp. 549-572, John Wiley & Sons, Inc.
Strobel, H.A. et al., *Chemical Instrumentation: A Systematic Approach*, 3rd Ed., (1989), pp. 391-393, 879-894, 922-925, 953.
Anonymous, "N-[1-(R)-(-)(1-naphthyl)]-3-[3-[3-(trifluoromethyl)phenyl]-1-aminopropane hydrochloride", IP.COM Journal, May 23, 2005 (May 23, 2005), XP002424259.
Database Beilstein; Belistein Institute for Organic Chemistry, Frankfurt-Main, DE; XP002451055; abstract (& Pharmazie, vol. 59, No. 10, 2004, pp. 744-752).

*Primary Examiner*—Yvonne Eyler
*Assistant Examiner*—Sudhakar Katakam
(74) *Attorney, Agent, or Firm*—Kenyon & Kenyon LLP

(57) ABSTRACT

Provided is a process for preparing cinacalcet, (R)-α-methyl-N-[3-[3-(trifluoromethyl)phenyl]propyl]-1-naphthalenemethane amine.

20 Claims, No Drawings

PROCESS FOR THE PREPARATION OF CINACALCET BASE

CROSS-REFERENCE TO RELATED APPLICATIONS

This application claims the benefit of priority to U.S. provisional application Ser. Nos. 60/799,443, filed May 10, 2006, and 60/796,317, filed Apr. 27, 2006, hereby incorporated by reference.

FIELD OF THE INVENTION

The invention encompasses a process for preparing cinacalcet, (R)-α-methyl-N-[3-[3-(trifluoromethyl)phenyl]propyl]-1-naphthalenemethane amine.

BACKGROUND OF THE INVENTION (R)-α-methyl-N-[3-[3-(trifluoromethyl)phenyl]propyl]-1-naphthalenemethane amine ("CNC-base," "cinacalcet base," or "cinacalcet") has the following formula:

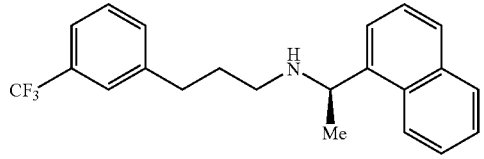

and a CAS number of 226256-56-0. This molecule is the free base form of cinacalcet hydrochloride, $C_{22}H_{22}F_3N \cdot HCl$. Cinacalcet hydrochloride ("CNC—HCl"), has a molecular weight of 393.9 and CAS number 364782-34-3. CNC—HCl is marketed as SENSIPAR™, and is the first drug in a class of compounds known as calcimimetics to be approved by the FDA.

Calcimimetics are a class of orally active, small molecules that decrease the secretion of parathyroid hormone ("PTH") by activating calcium receptors. The secretion of PTH is normally regulated by the calcium-sensing receptor. Calcimimetic agents increase the sensitivity of this receptor to calcium, which inhibits the release of parathyroid hormone, and lowers parathyroid hormone levels within a few hours. Calcimimetics are used to treat hyperparathyroidism, a condition characterized by the over-secretion of PTH that results when calcium receptors on parathyroid glands fail to respond properly to calcium in the bloodstream. Elevated levels of PTH, an indicator of secondary hyperparathyroidism, are associated with altered metabolism of calcium and phosphorus, bone pain, fractures, and an increased risk for cardiovascular death.

CNC—HCl is approved for treatment of secondary hyperparathyroidism in patients with chronic kidney disease on dialysis. Treatment with CNC—HCl lowers serum levels of PTH as well as the calcium/phosphorus ion product, a measure of the amount of calcium and phosphorus in the blood.

U.S. Pat. No. 6,011,068 discloses calcium receptor-active molecules, such as those having the general structure of cinacalcet. U.S. Pat. No. 6,211,244 ("'244 patent") discloses calcium receptor-active compounds related to cinacalcet and methods of preparing such compounds. Using the methods disclosed in the '244 patent, as well as DRUGS OF THE FUTURE (2002) 27(9):831, the desired cinacalcet enantiomer, may be produced by reacting 3-[3-(trifluoromethyl)phenyl]propylamine with 1-acetyl naphthalene in the presence of titanium (IV) isopropoxide, to produce an imine corresponding to cinacalcet, followed by treatment with ethanolic or methanolic sodium cyanoborohydride, and resolution of the racemic cinacalcet by chiral liquid chromatography, as depicted in the following scheme:

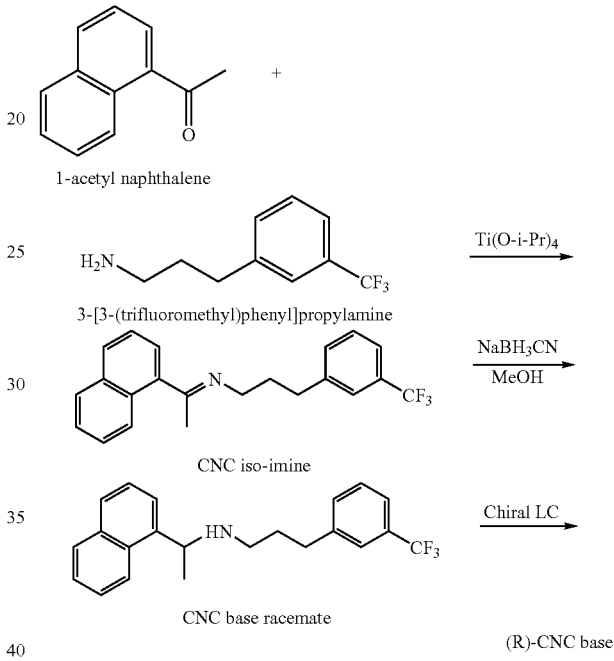

However, this process involved the use of flammable and highly toxic reagents, such as titanium (IV) isopropoxide and ethanolic or methanolic sodium cyanoborohydride.

In another process disclosed in the '244 patent, cinacalcet may be produced by treating 3-trifluoromethylcinnamonitrile with diisobutyl aluminum hydride, followed by treatment of the intermediate aluminum-imine complex with (R)-1-(1-naphthyl)ethylamine, and reduction of the intermediate imine with ethanolic sodium cyanoborohydride, according to the following scheme:

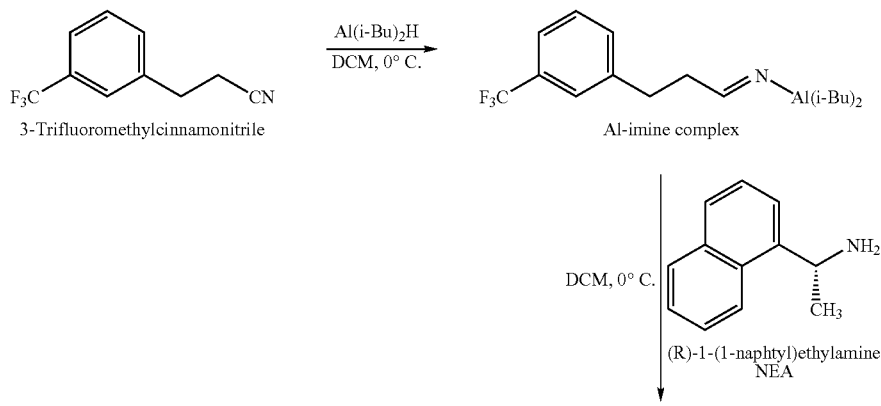

(R)-CNC base $\xleftarrow[\text{EtOH, RT}]{\text{NaBH}_3\text{CN}}$ 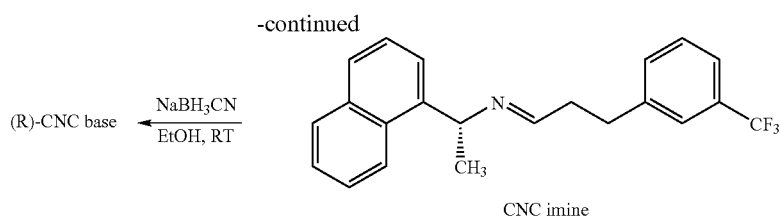

CNC imine

Synthesis of the 3-trifluoromethylcinnamonitrile precursor in this process is disclosed only in Tetrahedron Letters (2004) 45:8355. Although this is a possible process, Al[iBu] is highly flammable and, thus, this process is not ideal.

Similarly, using the process disclosed in the '244 patent, as well as DRUGS OF THE FUTURE (2002) 27 (9): 831, the desired cinacalcet enantiomer may be produced by reacting (R)-1-(1-naphthyl)ethylamine with 3-[3-(trifluoromethyl)phenyl]pro-pionaldehyde in the presence of titanium (IV) isopropoxide to produce the imine that corresponds to cinacalcet, followed by treatment with ethanolic sodium cyanoborohydride, according to the following scheme:

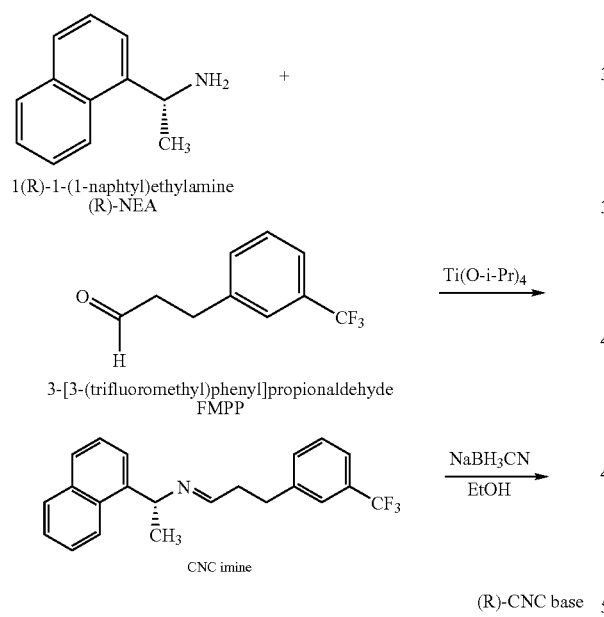

However, the processes mentioned require the use of reagents such as titanium (IV) isopropoxide and ethanolic sodium cyanoborohydride, which are highly flammable, difficult to handle and toxic. Moreover, the only synthetic route known to the precursor of CNC-base, 3-[3-(trifluoromethyl) phenyl]propionaldehyde is disclosed in Tetrahedron Letters (2004) 45: 8355, and is described in the following scheme:

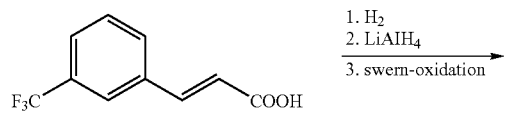

1. H$_2$
2. LiAlH$_4$
3. swern-oxidation

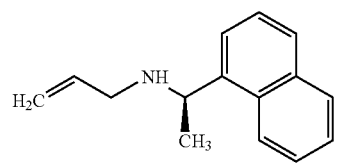

by reduction of the double bond of the corresponding cinnamic acid derivative, followed by reduction of the carboxylic acid moiety to the corresponding alcohol, which is then oxidized to the aldehyde by Swern-oxidation, using reagents which are not environmentally friendly reagents and are unstable, such as oxalyl chloride and dimethyl sulfoxide.

Thus, there is a need in the art for an improved process for the preparation of CNC-base and salts thereof, preferably, the hydrochloride salt, that is more environmentally friendly. The present invention provides such an alternative.

SUMMARY OF THE INVENTION

In one embodiment, the invention encompasses a process for preparing cinacalcet comprising: (a) combining 3-bromotrifluorotoluene with an allyl amine of the following formula I

I

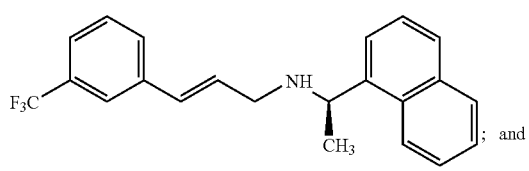

in the presence of a catalyst and at least one base; (b) heating the combination to obtain unsaturated cinacalcet base of the following formula II

II

; and (c) reducing the unsaturated cinacalcet base of formula II to obtain cinacalcet.

In another embodiment, the invention encompasses a process for preparing a pharmaceutically acceptable salt of cinacalcet comprising: (a) preparing cinalcalcet by the above-described process; and (b) converting the cinacalcet into a pharmaceutically acceptable salt of cinacalcet.

DETAILED DESCRIPTION OF THE INVENTION

The invention addresses the above-described shortcomings of the prior art by providing an improved process for preparing cinacalcet base. The process can be illustrated by the following general scheme:

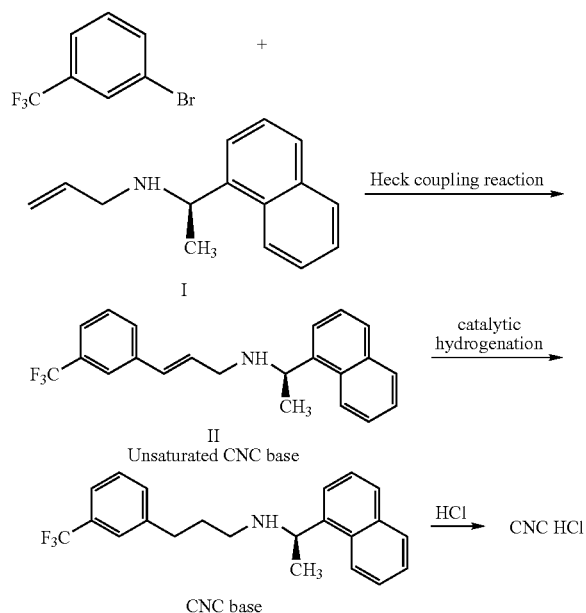

I

II
Unsaturated CNC base

CNC base

The process comprises: (a) combining 3-bromotrifluorotoluene ("3-BrTFT") with an allyl amine of the following formula I

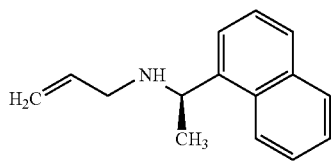

I in the presence of a catalyst and at least one base; (b) heating the combination to obtain unsaturated cinacalcet base of the following formula II

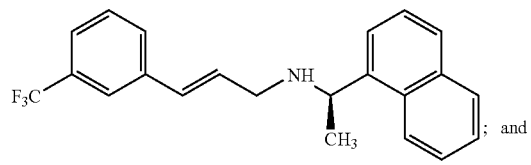

II

; and (c) reducing the unsaturated cinacalcet base of formula II to obtain cinacalcet base.

Typically, the 3-BrTFT is provided in the form of a solution in any solvent in which it dissolves. Preferably, the solvent is 1-methyl-2-pyrrolidinone (NMP), acetonitrile, toluene, N,N-dimethyl formamide (DMF) or a mixture of DMF and water. Typically, the solution contains 3-BrTFT in a concentration of about 3.5 to about 5.0 grams per mole of solvent.

Typically, the allyl amine of formula I is present in an amount of about 1 to about 1.5 moles per mole of 3-BrTFT. Preferably, the allyl amine of formula I is present in an amount of about 1.2 moles per mole of 3-BrTFT.

The catalyst may be any catalyst suitable for a Heck coupling reaction, such as palladium/carbon (Pd/C) in extrudate or powder form or palladium acetate [Pd(OAc)$_2$]. Preferably, the catalyst is palladium/carbon and more preferably the palladium/carbon is in powder form. The catalyst may be in an amount of about 20-50% water by weight. Preferably, in addition to the palladium/carbon or palladium acetate [Pd(OAc)$_2$], a triphenylphosphine or tri-(ortho-tolyl) phosphine may be added in a catalytic amount.

The base may be any base capable of neutralizing the hydrogen bromide formed during the Heck coupling reaction. Suitable bases include, but are not limited to, mono-, di-, tri-$C_1$ to $C_4$ alkyl amines and alkali metal bases. More specific examples include $K_2CO_3$, $Na_2CO_3$, KOAc, NaOAc, and trialkyl amines such as $Et_3N$ ("TEA") and $Bu_3N$ ("TBA"). Preferably, the base is an alkali metal base, and more preferably potassium carbonate. It is worth noting that a skilled artisan will know to use an anhydrous nitrogen atmosphere for some bases, including potassium carbonate in certain cases, to prevent humid conditions.

Typically, the combination is heated at a temperature of about 81° C. to 145° C. Typically, the combination is heated for about 3 to about 24 hours to obtain a reaction mixture of the unsaturated cinacalcet base of formula II.

Typically, prior to step (c), the reaction mixture containing the unsaturated cinacalcet base of formula II is cooled and residual salts and catalysts are filtered from the reaction mixture. The filter cake is then washed and the solvent is removed from the filtrate under reduced pressure to obtain crude unsaturated cinacalcet base of formula II.

Alternatively, the unsaturated cinacalcet base of formula II thus obtained may be recovered from the reaction mixture by extraction prior to step (c). Preferably, the unsaturated cinacalcet base is extracted from the reaction mixture using a solvent selected from the group consisting of $C_{4-8}$ ethers, $C_{3-6}$ esters, $C_{5-8}$ cyclic, aromatic and aliphatic hydrocarbons and mixtures thereof. More preferably, the solvent is ethyl acetate, dichloromethane (DCM), toluene or mixtures thereof.

The unsaturated cinacalcet base of formula II obtained by any of the above methods is then reduced to obtain cinacalcet base. Preferably, the unsaturated cinacalcet base of formula II is reduced by catalytic hydrogenation (i.e., with hydrogen in the presence of catalyst).

The catalytic hydrogenation may be performed by any method known to one of ordinary skill in the art. For example, the unsaturated cinacalcet base may be dissolved in a lower alcohol, i.e., a $C_1$-$C_4$ aliphatic, straight chain or branched alcohol, and exposed to $H_2$ pressure in the presence of a catalyst such as Pd/C or $PtO_2$ (Adam's catalysts) or Raney nickel. When Pd/C or $PtO_2$ is used, the $H_2$ pressure is typically 1 atmosphere. When Raney nickel is used, the $H_2$ pressure is moderately high (~1000 psi). Typically, the hydrogenation is carried out over a period of about 5 to about 24 hours to obtain cinacalcet base.

Optionally, the obtained cinacalcet base may be converted into a pharmaceutically acceptable salt of cinacalcet by any method known to one of ordinary skill in the art. A preferred pharmaceutically acceptable salt is the hydrochloride salt.

The hydrochloride salt may be prepared by a method including, but not limited to, reacting the cinacalcet base with hydrogen chloride. Typically, the cinacalcet base is dissolved in an organic solvent and combined with aqueous or gaseous hydrogen chloride to obtain cinacalcet hydrochloride. Preferably, the organic solvent is ethanol, toluene, or methyl tert-butyl ether ("MTBE").

Having thus described the invention with reference to particular preferred embodiments and illustrative examples, those in the art would appreciate modifications to the invention as describes and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinal skill in the art and are described in numerous publications. All references mentioned herein are incorporated in their entirety.

EXAMPLES

Example 1

Preparation of Cinacalcet Base a. Step 1: Preparation of Unsaturated Cinacalcet Base of Formula II A 500 ml 3-necked flask equipped with a magnetic stirrer, a thermometer, a gas inlet adaptor and a reflux condenser is flushed with $N_2$, and charged with 3-BrTFT (0.15 mol, 33.8 g), allyl amine of formula I (0.18 mol), $K_2CO_3$ (14.6 g), NMP (120 ml), and Pd/C (2%) ($7.5 \times 10^{-4}$ mol, 4.0 g). The resulting reaction mixture is flushed with $N_2$ for 15 minutes and then heated to 140° C. for 3 hrs. The reaction mixture is then cooled to room temperature and the residual catalyst and salts are filtered out. The filter cake is washed with 10 ml of NMP. The solvent is removed from the filtrate under reduced pressure (12 mmHg) with heating (87° C.) to obtain crude unsaturated cinacalcet base of formula II.

b. Step 2: Reduction of Unsaturated Cinacalcet Base of Formula II to Obtain Cinacalcet Base The crude unsaturated CNC base produced in step 1 is dissolved in absolute ethanol (5 volumes per gram of unsaturated CNC base) and hydrogenated (1 atm of $H_2$) in the presence of palladium on carbon (10% w/w of starting material) for 16 hours at room temperature. Then the catalyst is filtered out and the solvent is evaporated until dryness to obtain cinacalcet base.

Example 2

Conversion of Cinacalcet Base to Cinacalcet Hydrochloride

Cinacalcet base is dissolved in absolute ethanol (4 volumes per gram of cinacalcet base). Then 1N HCl (1.5 eq.) is added drop-wise. The obtained mixture is stirred at room temperature for 20 hours to obtain a precipitate. The product is isolated by filtration, washed with water, and dried in a vacuum oven at 50° C. for 24 hours to obtain Cinacalcet hydrochloride.

Example 3

Conversion of Cinacalcet Base to Cinacalcet Hydrochloride

Cinacalcet base is dissolved in MTBE (20 volumes per gram of cinacalcet base). Then HCl gas (2 eq.) is bubbled into the solution at room temperature. The obtained slurry is stirred for 2 hours at room temperature. The product is isolated by filtration, washed with MTBE, and dried in a vacuum oven at 50° C. for 24 hours to obtain cinacalcet hydrochloride.

I claim:

1. A process for preparing cinacalcet comprising:
a) combining 3-bromotrifluorotoluene with an allyl amine of the following formula I

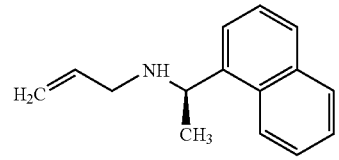

in the presence of a catalyst and at least one base;
b) heating the combination to obtain unsaturated cinacalcet base of the following formula II

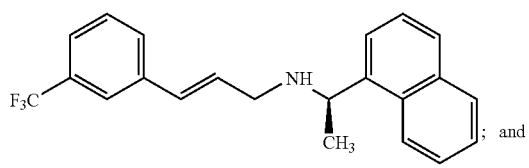

; and c) reducing the unsaturated cinacalcet base of formula II to obtain cinacalcet.

2. The process of claim 1, wherein the 3-bromotrifluorotoluene is dissolved in a solvent prior to combining with the allyl amine of formula I.

3. The process of claim 2, wherein the solvent is 1-methyl-2-pyrrolidinone, acetonitrile, toluene, N,N-dimethyl formamide, or a mixture of N,N-dimethyl formamide and water.

4. The process of claim 2, wherein about 3.5 to about 5.0 grams of 3-bromotrifluorotoluene are dissolved per mole of solvent.

5. The process of claim 1, wherein the allyl amine of formula I is present in an amount of about 1 to about 1.5 moles per mole of 3-bromotrifluorotoluene.

6. The process of claim 1, wherein the allyl amine of formula I is present in an amount of about 1.2 moles per mole of 3-bromotrifluorotoluene.

7. The process of claim 1, wherein the catalyst comprises palladium on carbon or palladium acetate.

8. The process of claim 7, wherein the catalyst further comprises a triphenylphosphine or tri-(ortho-tolyl)phosphine.

9. The process of claim 1, wherein the base is a mono-, di-, or tri-$C_1$ to $C_4$ alkyl amine or an alkali metal.

10. The process of claim 1, wherein the base is an alkali metal base.

11. The process of claim 1, wherein the base is potassium carbonate.

12. The process of claim 1, wherein the combination is heated at a temperature of about 81° C. to 145° C.

13. The process of claim 1, wherein the combination is heated for about 3 to about 24 hours.

14. The process of claim 1, wherein the unsaturated cinacalcet base of formula II is reduced with hydrogen in the presence of a catalyst.

15. The process of claim 14, wherein the catalyst is palladium on carbon, platinum dioxide, or Raney nickel.

16. The process of claim 14, wherein the reduction is performed over a period of about 5 to about 24 hours.

17. The process of claim 14, wherein the hydrogen is present at a pressure of about 1 atmosphere to about 1000 psi.

18. A process for preparing a pharmaceutically acceptable salt of cinacalcet comprising:
   a) preparing cinacalcet by the process of claim 1; and
   b) converting the cinacalcet into a pharmaceutically acceptable salt of cinacalcet.

19. The process of claim 18, wherein the pharmaceutically acceptable salt is the hydrochloride salt.

20. The process of claim 19, wherein the cinacalcet is converted into the hydrochloride salt by combining the cinacalcet with hydrogen chloride.

* * * * *